United States Patent [19]

Makryaleas et al.

[11] Patent Number: 5,591,613
[45] Date of Patent: *Jan. 7, 1997

[54] METHOD FOR THE PREPARATION OF D-ARGININE AND L-ORNITHINE

[75] Inventors: Kyriakos Makryaleas, Radolfzell; Karlheinz Drauz, Freigericht; Andreas Bommarius, Frankfurt/M, all of Germany

[73] Assignee: Degussa Aktiengesellschaft, Frankfurt am Main, Germany

[ * ] Notice: The term of this patent shall not extend beyond the expiration date of Pat. No. 5,405,761.

[21] Appl. No.: 366,544

[22] Filed: Dec. 29, 1994

Related U.S. Application Data

[63] Continuation-in-part of Ser. No. 715,963, Jun. 17, 1991, Pat. No. 5,405,761.

[30] Foreign Application Priority Data

Jul. 2, 1990 [DE] Germany .......................... 40 20 980.6

[51] Int. Cl.⁶ ....................................................... C12P 13/10
[52] U.S. Cl. ............................................. 435/114; 435/227
[58] Field of Search ................................... 435/114, 227; 562/554, 560

[56] References Cited

U.S. PATENT DOCUMENTS

| | | | |
|---|---|---|---|
| 3,222,258 | 12/1965 | Iizuka | 435/114 |
| 3,668,072 | 6/1972 | Ando | 435/114 |
| 4,248,677 | 2/1981 | Kato | 562/560 |
| 4,346,169 | 8/1982 | Akashi | 435/114 |
| 4,420,432 | 12/1983 | Chibata | 260/501.11 |
| 4,698,442 | 10/1987 | Nestor | 562/560 |
| 5,059,712 | 10/1991 | Griffith | 562/560 |
| 5,405,761 | 4/1995 | Makryaleas | 435/114 |

*Primary Examiner*—Irene Mark
*Attorney, Agent, or Firm*—Cushman Darby & Cushman IP Group of Pillsbury Madison & Sutro LLP

[57] ABSTRACT

D-arginine and L-ornithine are prepared by means of the enzymatic conversion of DL-arginine in the presence of an L-arginase which selectively converts L-arginase to L-ornithine, permitting recovery of both D-arginine and L-ornithine.

5 Claims, 6 Drawing Sheets

METHOD FOR THE PREPARATION OF D-ARGININE AND L-ORNITHINE

This is a continuation-in-part of U.S. application of Makryaleas, et al., Ser. No. 07/715,963, filed Jun. 17, 1991 which issued as U.S. Pat. No. 5,405,761 on Apr. 11, 1995.

The present invention relates to a method for the preparation of D-arginine, along with salts of L-ornithine, by means of the enzymatic conversion of DL-arginine into L-ornithine, in the presence of the enzyme L-arginase (E.C.3.5.3.1), in an aqueous medium and by means of a subsequent formation of the L-ornithine salt. During the process, L-arginine is selectively converted to L-ornithine, and D-arginine is recovered in purified form.

BACKGROUND OF THE INVENTION

Salts of L-ornithine are valuable pharmaceutical products. They are useful, e.g., for parenteral nutrition (L-ornithine acetate or L-ornithine monohydrochloride) and the treatment of hepatic diseases (L-ornithine aspartate or L-ornithine-2-ketoglutarate). L-ornithine can replace L-arginine, an amino acid which is essential in infants and children, in all functions. A deficiency of arginine or ornithine can result in damage up to death, e.g. by means of a super-elevated ammonia level after the take-up of amino acid after a period of fasting or of malnourishment (so-called protein shock). L-ornithine therefore has considerable commercial potential.

L-arginase is an enzyme which catalyses the hydrolysis of L-arginine to L-ornithine and urea in the urea cycle of higher mammals. It can be isolated from the livers of various higher mammals such as the cow, calf or rat and was primarily used in the past for diagnostic purposes.

As is known, L-arginase exhibits a narrow substrate spectrum, so that, in addition to L-arginine, only few analogues are converted. However, almost all research concentrated in the past on levorotary (L-) compounds. L-arginine is obtained today almost exclusively from biological sources such as fermentation or protein hydrolyzates. No D-arginine forms in these two methods. Only a little testing has been performed on D-arginine as a substrate, with varying results (D. Kavanaugh, M. A. Berge and G. A. Rosenthal, *Plant Physiol.* 1990, 94, 67–70; G. Muszynska, L. O. Severina and L. V. Lobyreva, *Acta Biochim. Pol.* 1972, 19, 109–116). DL-arginine, accessible by means of the chemical racemization of L-arginine, has not yet been investigated as a potential substrate of L-arginase, that is, the enantioselectivity of arginase was previously unknown. It also was not known in the past whether D-arginine exerts an inhibitory action on arginase.

D-arginine also is a useful product in its own right. Thus, there is an increasing demand for synthetic D-Arginine for use in the manufacture of pharmaceutical peptides such as LHRH antagonists. Like many D-amino acids, it is not so readily attacked by enzymes in the body as the natural analogues.

L-ornithine is advantageously obtained from L-arginine in industry by the same reaction as in the body of mammals. During the enzymatic process, L-arginase (L-arginine amidino hydrolase, E.C. 3.5.3.1.) from mammal livers is used. In addition to the enzymatic method, the fermentation from glucose by means of the strains Brevibacterium, Corynebacterium and Arthrobacter, as well as the chemical hydrolysis of L-arginine can be used as synthetic methods for producing L-ornithine and its salts.

The enzymatic process has distinct advantages over the alternatives:

The market is too small for the fermentative route;

The chemical hydrolysis of L-arginine results in side reactions, e.g. racemization or deiminization to citrulline.

A disadvantage of the enzymatic process consisted until recently in the limited availability of arginase since the enzyme was used only in diagnostics. However, several firms have been offering the enzyme for a few years now, in some instances in the raw form.

SUMMARY OF THE INVENTION

The present invention provides a method for the enzymatic conversion of DL-arginine in the presence of an L-arginase enzyme (E.C.3.5.3.1) which selectively converts L-arginase into L-ornithine. The enzymatic conversion is carried out in an aqueous medium in which the pH required for the enzymatic conversion is maintained in a range of 8.0 to 10.0, preferably with the acid whose L-ornithine salt is to be prepared. The D-arginine is separated after the end of the enzymatic conversion, then the pH is adjusted to the range 6.5 to 7.0 with the same acid and the L-ornithine salt formed is isolated directly from the reaction mixture.

It is especially advantageous if the enzyme is separated from the reaction mixture by ultrafiltration before the isolation of the L-ornithine salt.

During the practical operation of the method of the invention, the original pH of the aqueous arginine solution of approximately 11.0 is first adjusted with an acid, preferably the acid whose L-ornithine salt is to be prepared, to a pH in a range of 8.0 to 10.0. Then, it is advantageous to add a small amount of a salt of a bivalent metal in order to achieve a high activity of the enzyme. An addition of $Mn^{2+}$ salts in a $10^{-3}$ to $10^{-5}$ molar concentration is especially suitable. After the addition of the L-arginase, the enzymatic conversion is carried out at a temperature between 5° C. and 50° C., preferably between 20° C. and 35° C. The reaction time required is a function of the amount of enzyme used and is generally between 5 and 48 hours. The arginine is advantageously used in a concentration of 5 to 40% by weight.

Although DL-arginine with the same portions of D- and L-enantiomers is readily obtainable by means of the racemization of L-arginine, the ratio of D- and L-arginine does not necessarily have to be 1:1 in the present method. The reaction can also start from an excess of one of the two enantiomers. Although the reaction also takes place in the presence of solid arginine, it is nevertheless carried out with advantage in homogenous solution, since, otherwise, a complete conversion of the L-arginine in the undispersed sediment is not assured.

After concluding the reaction the enzyme can be separated by ultrafiltration from the products produced and then be reused for the next batch. The unreacted D-arginine must be separated after the conclusion of the enzymatic conversion and prior to the neutralization of the reaction mixture, from the L-ornithine which has formed. This can take place e.g. by means of ion exchange chromatography. The ultrafiltered product solution is put onto an ion-exchange column with strongly basic resin, e.g. Lewatit M 500 or M 600. The more basic ornithine is bound on the column by the resin, whereas the arginine can be collected at the outlet. The arginine can then be precipitated from the aqueous solution by the addition of alcohol, filtered off and dried.

The ornithine can be eluted from the column with dilute acid, during which a pH of 3 to 7 should be maintained. Subsequently, excess acid and water are drawn off on a rotary evaporator or a falling-film evaporator, if possible, and the ornithine salt precipitated, if necessary after clarification with activated carbon, from an alcohol, e.g., methanol and especially ethanol. Examples of acids which can be used are hydrochloric acid (to obtain L-ornithine hydrochloride), sulfuric acid (to obtain L-ornithine sulfate), L-aspartic acid (to obtain L-ornithine aspartate), phosphoric acid (to obtain L-ornithine phosphate) or acetic acid (to obtain L-ornithine acetate (German Patent 40 20 980, 1991).

Practically any salts of L-ornithine can be prepared by means of the method of the invention. They can be the salts of inorganic acids such as hydrochloric acid, sulfuric acid or phosphoric acid. However, the method of the invention is especially suited for the preparation of the salts of L-ornithine with organic acids. Suitable organic acids are e.g. saturated aliphatic monocarboxylic acids such as formic acid, acetic acid or propionic acid; unsaturated aliphatic monocarboxylic acids such as oleic acid, linoleic acid or linolenic acid; functionalized acids such as hydroxycarboxylic acids (e.g. lactic acid or mandelic acid), ketocarboxylic acids (e.g. α-ketoglutaric acid), amino carboxylic acids (e.g. asparaginic acid, glutamic acid or pyroglutamic acid); saturated aliphatic dicarboxylic acids such as succinic acid or adipic acid; unsaturated aliphatic dicarboxylic acids such as maleic acid or fumaric acid; aromatic carboxylic acids such as salicylic acid; araliphatic carboxylic acids such as phenylacetic acid, phenylpropionic acid or cinnamic acid; or functionalized di- and tricarboxylic acids such as malic acid or citric acid.

Surprisingly, no inhibition or deactivation of the enzyme occurs when using the very varied acids for adjusting the pH necessary for the enzymatic conversion. As a consequence, the very varied salts of L-ornithine can be prepared in a simple manner and in high yield in accordance with the method of the invention.

The L-arginase used is one which selectively converts L-arginine into L-ornithine, and does not convert the D-arginine component of DL-arginine. The preferred form of enzyme is L-arginase (E.C.3.5.3.1) which is isolated from animal liver, especially beef or calf liver, and it can be used both in its natural form as well as in a suitable stabilized form. It is commercially available in both forms. On the other hand, phytogenic L-arginase (E.C.3.5.3.1), i.e., derived from plant sources, does not have the required selectivity.

DETAILED DESCRIPTION OF PREFERRED EMBODIMENTS

The method of the invention is illustrated in more detail by the following examples. The course of the enzymatic conversion can be followed via the determination of the L-ornithine formed or of the L-arginine consumed by means of chromatography. The formed salts are characterized by the specific rotation and by elemental analysis.

Examples 1–10 illustrate the enzymatic conversion with L-arginine employing methods which can be adapted to use with DL-arginine.

EXAMPLE 1

130.5 g L-arginine were stirred into 800 ml $H_2O$ and adjusted with α-ketoglutaric acid to pH=9.5. After the addition of 0.042 g $MnSO_4 \cdot H_2O$, the reactor was filled to 1,000 ml with $H_2O$. After the addition of 220 mg arginase, the reaction mixture was agitated 20 hours at room temperature.

Thereafter, the solution was neutralized with α-ketoglutaric acid and ultrafiltered for the purpose of enzyme separation, concentrated by evaporation in a rotary evaporator and compounded under cooling with ethanol, at which time the product crystallized out. With 166.6 g isolated (di-L-ornithine)-α-ketoglutarate dihydrate, the yield was 97%, relative to the L-arginine used. The isolated product had the following properties:
Content (titration): >99%
Specific rotation: $[\alpha]\ 20_D = +7.8°$ (c=5 in $H_2O$)

| Elemental analysis: | % C | % H | % N |
|---|---|---|---|
| Calculated: | 40.3 | 7.6 | 12.55 |
| Observed: | 39.13 | 8.08 | 14.06 |
| Drying loss: | 9.9% | | |
| Sulfate ash: | <0.1% | | |

EXAMPLE 2

The same method was used as in Example 1; however, 174.3 g L-arginine were added and L-aspartic acid was used to adjust the reaction pH and to neutralize the L-ornithine produced.

The isolated yield of L-ornithine-L-aspartate was 99% relative to L-arginine used. The isolated product had the following properties:
Content (titration): >99%
Specific rotation $[\alpha]\ 20_D = +28.0°$ (c=8 in 6N HCl)

| Elemental analysis: | % C | % H | % N |
|---|---|---|---|
| Calculated: | 40.71 | 7.31 | 15.83 |
| Observed: | 37.93 | 8.23 | 15.38 |
| Drying loss: | 0.3% | | |

EXAMPLE 3

The same method was used as in Example 1; however, 348.5 g L-arginine were added and L-glutamic acid was used to adjust the reaction pH and to neutralize the L-ornithine produced.

The isolated yield of L-ornithine-L-glutamate was 96.6% relative to L-arginine used. The isolated product had the following properties:
Content (titration): >99%
Specific rotation $[\alpha]\ 20_D = +30.4°$ (c=8 in 6N HCl)

| Elemental analysis: | % C | % H | % N |
|---|---|---|---|
| Calculated: | 42.99 | 7.52 | 15.04 |
| Observed: | 42.50 | 8.05 | 14.71 |
| Drying loss: | 0.7% | | |

EXAMPLE 4

The same method was used as in Example 1; however, L-pyroglutamic acid was used to adjust the reaction pH and to neutralize the L-ornithine produced. The isolated yield of L-ornithine-L-pyroglutamate monohydrate was 95.8% relative to L-arginine used. The isolated product had the following properties:

Content (titration): >99%
Specific rotation [α] $20_D$=+17.2 (c=8 in 6N HCl)

| Elemental analysis: | % C | % H | % N |
|---|---|---|---|
| Calculated: | 43.1 | 7.52 | 15.05 |
| Observed: | 43.45 | 8.07 | 15.08 |
| Drying loss: | 5.4% | | |

EXAMPLE 5

The same method was used as in Example 1; however, $H_2SO_4$ was used to adjust the reaction pH and to neutralize the L-ornithine produced. The isolated yield of (L-ornithine)$_2$-sulfate monohydrate was 93.9% relative to L-arginine used. The isolated product had the following properties:
Content (titration): >99%
Specific rotation [α] $20_D$=+8.2° (c=10 in $H_2O$)

| Elemental analysis: | % C | % H | % N |
|---|---|---|---|
| Calculated: | 31.57 | 7.4 | 14.73 |
| Observed: | 31.68 | 8.20 | 14.55 |
| Drying loss: | 4.4% | | |
| Sulfate ash: | 0.1% | | |

EXAMPLE 6

The same method was used as in Example 1; however, HCl was used to adjust the reaction pH and to neutralize the L-ornithine produced. The isolated yield of L-ornithine monohydrochloride was 97.4% relative to L-arginine used. The isolated product had the following properties:
Content (titration): >99%
Specific rotation [α] $20_D$=+23.8 (c=4 in 6N HCl)

| Elemental analysis: | % C | % H | % N |
|---|---|---|---|
| Calculated: | 35.58 | 7.71 | 16.6 |
| Observed: | 35.40 | 8.38 | 14.31 |

EXAMPLE 7

The same method was used as in Example 1; however, acetic acid was used to adjust the reaction pH and to neutralize the L-ornithine produced. The isolated yield of L-ornithine acetate was 95.4% relative to L-arginine used. The isolated product had the following properties:
Content (titration): >99%
Specific rotation [α] $20_D$=+10.0° (c=5 in $H_2O$)

EXAMPLE 8

The same method was used as in Example 1; however, D-mandelic acid was used to adjust the reaction pH and to neutralize the L-ornithine produced. The isolated yield of L-ornithine-D-mandelate dihydrate was 94.2% relative to L-arginine used. The isolated product had the following properties:
Content (titration): >99%
Specific rotation [α] $20_D$=−52.7° (c=2 in $H_2O$)

| Elemental analysis: | % C | % H | % N |
|---|---|---|---|
| Calculated: | 48.75 | 7.5 | 8.75 |
| Observed: | 49.50 | 7.7 | 8.85 |
| Drying loss: | 9.4% | | |

EXAMPLE 9

The same method was used as in Example 1; however, phosphoric acid was used to adjust the reaction pH and to neutralize the L-ornithine produced. The isolated yield of (L-ornithine)$_3$-phosphate monohydrate was 93.1% relative to L-arginine used. The isolated product had the following properties:
Content (titration): >99%
Specific rotation [α] $20_D$=+20.4° (c=8 in 6N HCl)

| Elemental analysis: | % C | % H | % N |
|---|---|---|---|
| Calculated: | 35.1 | 8.0 | 16.4 |
| Observed: | 30.19 | 7.47 | 14.7 |
| Drying loss: | 3.7% | | |

EXAMPLE 10

The same method was used as in Example 1; however, glutathione in the form of the disulfide (GSSG) was used to adjust the reaction pH and to neutralize the L-ornithine produced. The isolated yield of (L-ornithine)$_2$-glutathione disulfide dihydrate was 97.7% relative to L-arginine used. The isolated product had the following properties:
Content (titration): >99%
Specific rotation [α] $23_D$=−70.3° (c=1.9 in $H_2O$)

| Elemental analysis: | % C | % H | % N |
|---|---|---|---|
| Calculated: | 38.4 | 6.14 | 14.34 |
| Observed: | 37.7 | 7.32 | 14.82 |
| Drying loss: | 5.4% | | |

In further experiments, the materials used were: Calf liver arginase (activity 110 U/mg) which was obtained from Boehringer Mannheim (Mannheim, F.R.G.). Amino acids were from Rexim (Ham, France). $MnSO_4$, $MnO_2$, and ascorbic acid were from E. Merck (Darmstadt, F.R.G.).

Batch conditions used were: Starting pH value, except for the activity-pH curve, was either 11.5, the natural value for L-Arg in water, or 9.5, adjusted from pH 11.5 with conc. HCl. The temperature was 25° C. unless otherwise noted. Typical concentrations of L-Arg were 0.75M. Unless otherwise mentioned, [Mn$^{2+}$]=5–10$^{-4}$M. Reaction progress was followed by HPLC (amino column, mobile phase: phosphate buffer (pH 6.4)/acetonitrile).

Kinetic data was obtained as follows: Initial rate data were analyzed by a non-linear regression method (Marquardt routine) with the program OPTI (U. Giesecke, KFA Jülich).

Determination of enantioselectivity was as follows: The enantioselectivity of arginase was determined by measuring concentrations of D-Arg, L-Arg, D-Orn and L-Orn simultaneously by HPLC (Crownpak CRY column). Enantioselectivity of enzymatic reactions is expressed by the E-value (See Chen, C. S., Y. Fujimoto, G. Girdaukas and C. Sih, *J. Amer. Chem. Soc.* 104 7294–99, (1982) (Equation 3):

$$E = \frac{\ln([\text{L—Arg}]/[\text{L—Arg}]_0)}{\ln([\text{D—Arg}]/[\text{D—Arg}]_0)}$$

The E value for a completely enantio-nonspecific reaction equals one; the higher the E-value the more enantiospecific the enzyme with regard to a pair of enantiomers of substrates and products.

Separation and work-up of D-Arg and L-Orn: After the arginase reaction, the D-Arg/L-Orn solution (100 ml) was transferred to an ion exchange column which contained a basic resin (Lewatit M600) (Resin volume 130 ml, height of bed 17 cm, capacity of column 0.7 mol/l resin). The Arg front elutes after about 50 ml at pH 11.5. The next 800 ml contained only Arg and urea according to HPLC. The solution was clarified with charcoal and concentrated on a rotary evaporator to 20 ml. Arg was precipitated with 3 to 5 volumes of isopropanol, filtered, washed and dried under vacuum at 60° C. The dried mother liquor also contains Arg as by-product along with urea as the main component.

Orn was eluted with 200 ml 5% acetic acid at a pH of 9.9 to 8.5 (Orn breaks through at about 150 ml). To form the acetate salt, equimolar amounts of glacial acetic acid were added (pH value reaches 6.9), the solution clarified with charcoal, and concentrated to 30 ml. L-Orn acetate was precipitated with three volumes of isopropanol and dried under vacuum at 60° C.

Temperature stability: 30 U/ml arginase were added to 0.75M L-Arg. After complete conversion after 24 hours, the enzyme solution was stored in water baths (±0.1° C.) at the designated temperature and pH 9.5 for defined lengths of time. An aliquot was added to fresh 0.75M L-Arg solution at pH 9.5 and 25° C. Conversion was measured after 2 hours and compared with the value at zero hours storage time.

Recycle reactor: On the lab scale, an enzyme membrane reactor (V=10 ml with flat membrane (polysulfone) and stirred compartments was employed; residence times τ were between 2.5 and 4 hours. On the pilot scale, a recycle reactor (V=12 liters) with a hollow-fiber UF module (2.5 m² (Romicon), polysulfone) was used; residence time τ was 3 hours. Reactions conditions were as mentioned above.

Operational enzyme stability: The basis for measuring operational enzyme stability has been described in C. Wandrey, Habilitationschrift, TH Hannover, Hannover Germany and A. S. Bommarius in *Bioprocessing*, Vol. 3, (ed: G. N. Stephanopoulos) *Series Biotechnology* (eds. H.-J. Rehn and G. Reed) 2d ed., VCH Publ., Weinheim, Basel, Deerfield Beach, Ch. 17, 1993, 427–66. The relevant criterion for enzyme stability in a process is the operational stability, conveniently measured in a recycle reactor operated as a CSTR with defined residence time τ, initial substrate concentration $[S]_o$, and initial enzyme concentration $[E]_o$.

In the course of the reaction, the enzyme deactivates, i.e. [E] decreases. To keep the degree of conversion constant, either fresh enzyme has to be added, effectively bringing [E] back up to $[E]_o$ or τ has to be increased to compensate for the decrease in active enzyme concentration due to inactivation. Choosing the first strategy, enzyme stability can be expressed as the amount of enzyme (in units or weight) consumed per unit mass of product.

Results

The results obtained using the foregoing procedures and materials were as follows:

Activity of arginase

Figure 1:
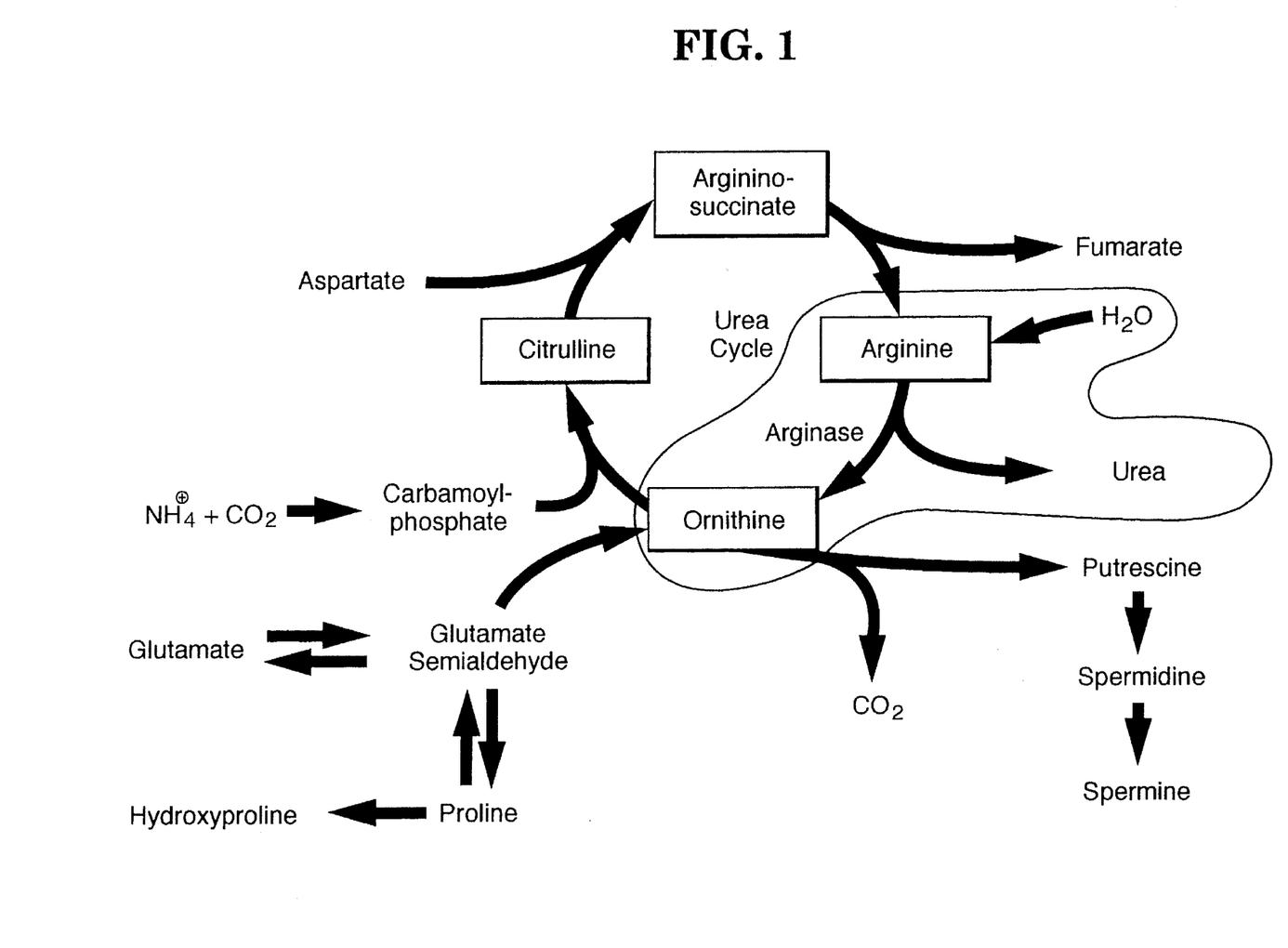
FIG. 1 shows the synthesis of L-ornithine as part of the mammalian urea cycle.
Figure 2:
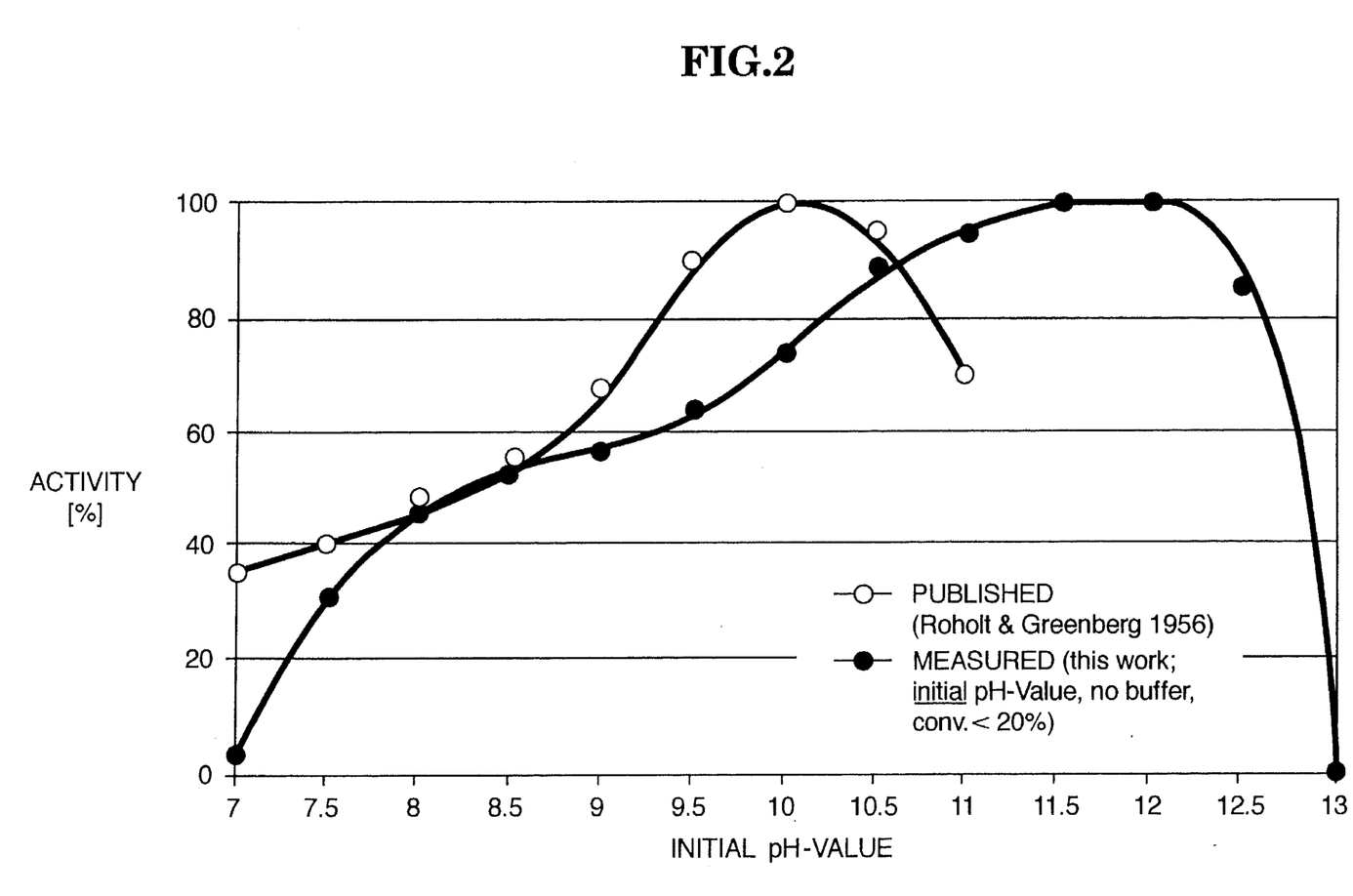
FIG. 2 is a graph, plotting activity of calf liver arginase vs. pH.

Activity-pH-profile: Calf liver arginase extends far more to the alkaline side than reported previously (FIG. 2). Maximum activity was found in the pH range between 11.0 and 12.0. Some other arginases show similar properties such as arginase from ox erythrocytes (pH optimum at 11.5). During most runs, no buffer was added to the L-Arg substrate solution to keep a low salt level for simplified separation and work-up of L-Orn product. Depending on initial concentration of L-Arg substrate, the initial pH is between 11.0 and 11.5, i.e. in the optimum pH range.

In the course of L-Arg hydrolysis to L-Orn, the pH decreases from around 11.5 to about 9.5. Even at pH 11.5, enzyme deactivation is slow enough not to cause significant damage. However, this work tested the hypothesis that arginase stability decreases with rising initial pH. Conversion of L-Arg to L-Orn by arginase does not necessitate addition of a buffer.

Activation by $Mn^{2+}$ ions and $MnO_2$ precipitation: An optimum concentration of the activator $Mn^{2+}$ of 0.5 mM was found. At the prevalent alkaline pH values, $MnO_2$ from the oxidation of $Mn^{2+}$ precipitates. To suppress oxidation, ascorbic acid was added as an reducing agent. It was found that ascorbate did not just prevent oxidation of $Mn^{2+}$ under many conditions, but it also seemed to influence arginase activity decay.

Figure 3:
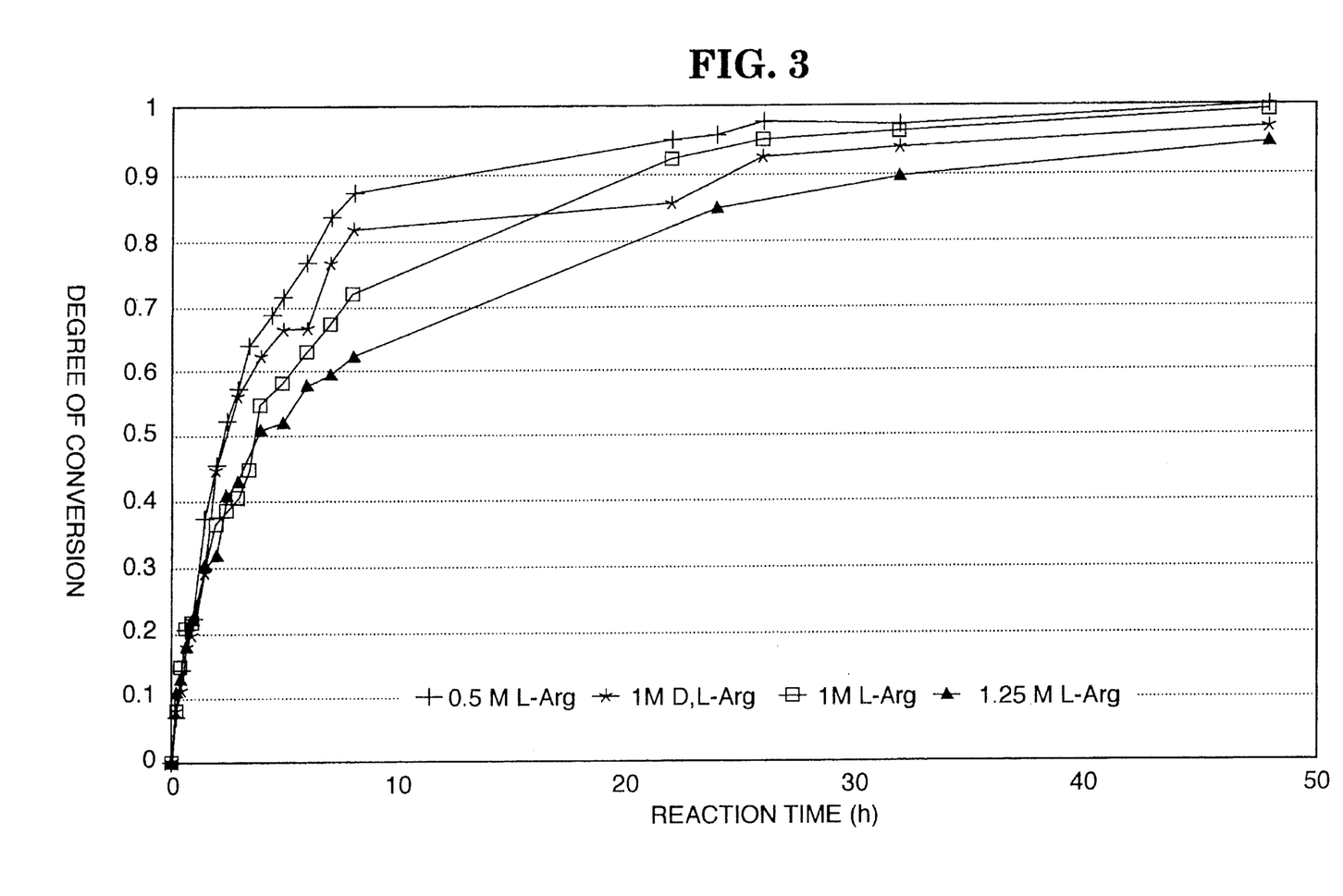
FIG. 3 is a graph showing conversion/time profiles of the arginase—catalyzed conversion of L-arginine into L-ornithine.

Kinetics: FIG. 3 depicts conversion vs. time profiles of the arginase-catalyzed conversion of L-Arg to L-Orn in a batch reactor; parameters are substrate concentration and L/D-ratio of Arg. In all cases, conversion to L-Orn is quantitative as expected from thermodynamics; however, at high substrate concentration or long residence time, a small amount of α-aminovalerolactam can be detected resulting from a cyclization reaction of L-Orn product following the desired transformation:

For all conversion-time profiles, the concentration of L-Arg was varied without the addition of buffer. The enzyme/substrate (L-Arg)-ratio was kept constant at 10 kUnits/(l·mol L-Arg). Thus, the profiles in FIG. 3 should all superimpose; deviations might be caused by pH variation at different substrate concentration and inhibition effects.

It can be inferred from the curves in FIG. 3 that L-Arg is not a substrate inhibitor. Since, especially at intermediate conversions, the rate decreases with increasing [L-Orn] but still reaches 100% conversion at long times the product most likely acts as a competitive inhibitor, in accordance with the literature. The reaction rate with L-Arg is also decreased in the presence of equal amounts of D-Arg (racemate). Attainment of complete conversion, in each case, also suggests competitive inhibition. By nonlinear regression of the initial rate data with L-Arg, $K_M$ was determined as 25.5 mM, $V_{max}$ as 459 Units (=μmol/(min·mg)). With typical [E] of 0.46 μM (MW=120 kD), $k_{cat}$ can be estimated as $1.2 \cdot 10^3$ s$^{-1}$. These data compare with $K_M$-values of 4.0 mM (29 mM for ox liver arginase) and $k_{cat}$-values of $6 \cdot 10^3$ s$^{-1}$ or $2.2 \cdot 10^3$ s$^{-1}$ ($1.17 \cdot 10^3$ s$^{-1}$ at pH 9.5 reported for the beef liver enzyme).

Figure 4:
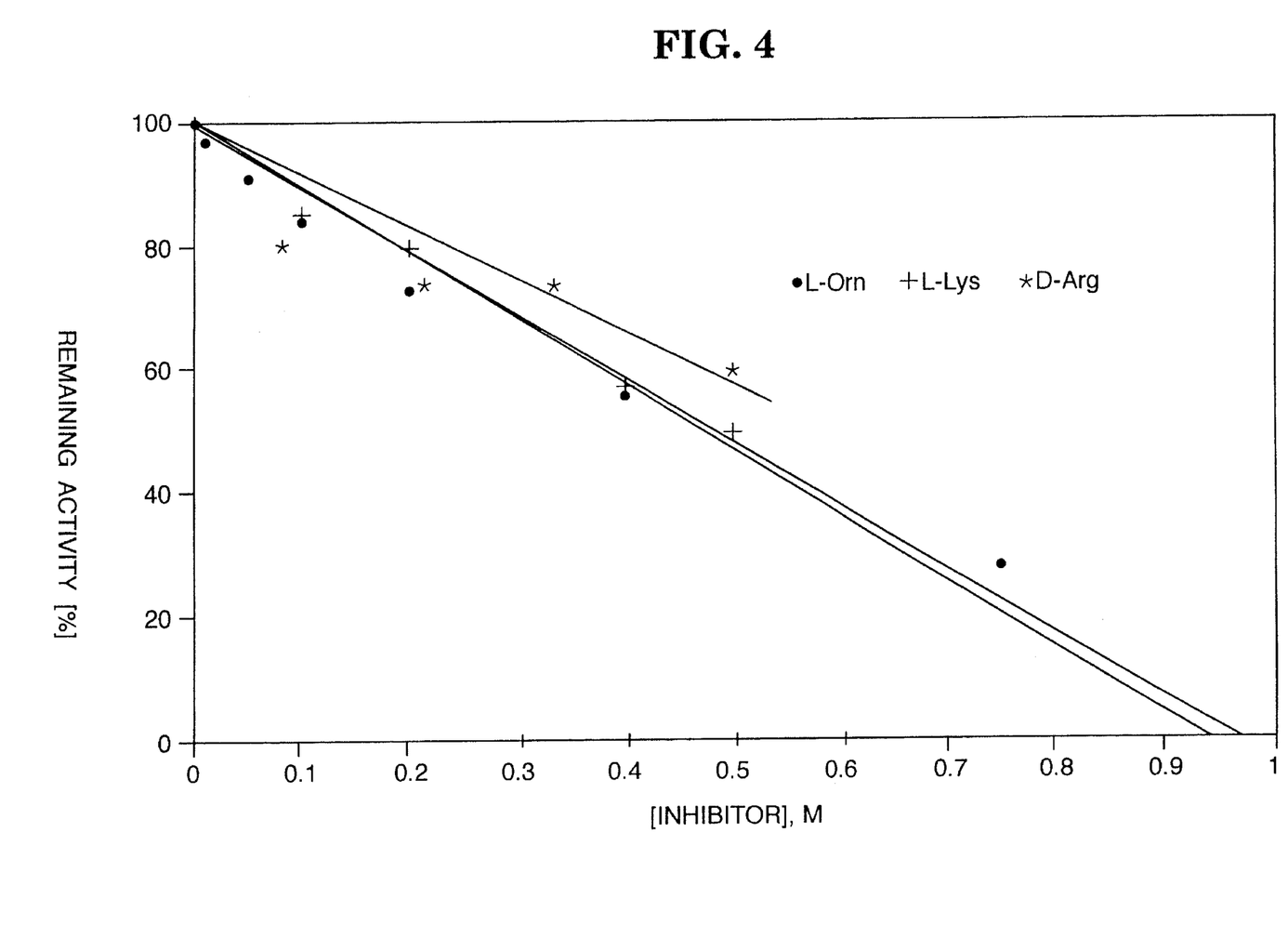
FIG. 4 is a plot of remaining activity vs. inhibitor concentration.

Inhibitors: L-Orn, L-Lys and D-Arg: The inhibitory effect of L-Orn and L-Lyg impurities which are often found in raw Arg solutions was studied further by plotting initial rates of a 50 mM L-Arg solution with specified amounts of inhibitor at the usual enzyme/substrate-ratio (Table 1 and FIG. 4).

TABLE 1

Effects of L-Orn and L-Lys on the hydrolysis of L-Arg

| (M) | conversion after 2 hrs. % | $V_{o\,Arginase}$ (mol/(l · hr) | $V_{o\,Arginase}$ (%) |
|---|---|---|---|
| [L-Orn] | | | |
| 0 | 40.2 | 0.151 | 100.0 |
| 0.01 | 39.0 | 0.146 | 97.0 |
| 0.05 | 36.6 | 0.137 | 91.0 |
| 0.1 | 28.5 | 0.107 | 70.9 |
| 0.2 | 24.1 | 0.090 | 60.0 |
| 0.4 | 22.3 | 0.084 | 55.5 |
| 0.75 | 11.3 | 0.042 | 28.1 |
| [L-Lys] | | | |
| 0 | 40.2 | 0.151 | 100.0 |
| 0.1 | 34.3 | 0.129 | 85.3 |
| 0.2 | 32.1 | 0.120 | 79.9 |
| 0.4 | 22.9 | 0.086 | 57.0 |
| 0.5 | 19.9 | 0.075 | 49.5 |
| 0.75 | 17.5 | 0.066 | 43.5 |

Cond: $5 \cdot 10^{-4}$ M $MnSO_4 \cdot H_2O$, $2.5 \cdot 10^{-4}$ M ascorbic acid, 0.75 M L-Arg, [E] = 10,000 Units/(l · mol L-Arg), $[S]_o/[E] = 1.63 \cdot 10^6$, starting pH: 11.5

A linear slope of 1/[S] vs. [I] plot distinguishes a purely competitive inhibition mechanism from a partially competitive one. Simultaneously, the apparent and the intrinsic $K_M$-value are proportional to [I] according to equation (5) from which the inhibition constant $K_I$ can be calculated $$K_{M,app} = K_{M,intr.}(1 + [I]/K_I) \quad (5)$$

Since the runs have been conducted at [LArg]=50 mM=$2 \cdot K_{m,intr}$, $V_o = V_{max} \cdot 2 \cdot K_{M,intr}/(K_{M,intr}(3+[I]/K_I)) = V_{max} \cdot 2/(3+[I]/K_I)$. At [I]=$K_I$, $V_o = V_{max} 2/(3+1) = V_{max}/2$. So, $K_I$ can be calcuated with sufficient accuracy from a $V_o$ vs. [I] plot such as FIG. 4. For L-Orn, $K_I$ is determined as 487 mM ($r^2$=0.985), for L-Lys, $K_I$ equals 484 mM ($r^2$=0.990), i.e., L-Orn and L-Lys are equally strong inhibitors. These values are far higher than those in the literature: 1.3 mM. At ordinary assay conditions, [L-Orn]<<$K_I$ so inhibitory effects are not observed. In this work, however, maximum product concentration was sought for optimal space-time-yield and work-up efficiency.

D-Arg has been tried as a substrate but not checked as a potential inhibitor. For the results in Table 2, [L-Arg] was kept constant at 500 mM while increasing amounts of D-Arg were added to cover the range from pure L-Arg to the racemate (D,L-Arg). While D-Arg certainly seems to inhibit the enzymatic hydrolysis of L-Arg, $K_{I\text{-}D\text{-}Arg}$ cannot be calculated according to the procedure applied for L-Orn and L-Lys because [S]=500 mM=$20 \cdot K_{M,intr}$ and thus $V_o$ is too close to $V_{max}$. A rough estimate from the initial rate data in Table 2 suggests that the inhibition constant for D-Arg might be around 600 to 800 mM, so even at the solubility limit of D,L-Arg (~1.25M) inhibition by equimolar amounts of D-Arg is not important.

TABLE 2

Influence of D-Arg on the hydrolsyis of L-Arg

| Ratio L/D-Arg | Arg- conf. | conversion (%) after | | | $r_{o, arginase}$ (mol/l/h) | $r_{o, arginase}$ % |
|---|---|---|---|---|---|---|
| | | 1.0 hrs | 1.5 hrs | 2.0 hrs | | |
| 100:0 | L | 37.4 | 40.7 | 45.6 | 0.187 | 100.0 |
| 85:15 | L(D) | 25.1 | 34.8 | 40.2 | 0.150 | 80.3 |
| 70:30 | L(D) | 24.6 | 31.8 | 35.4 | 0.1380 | 73.8 |
| 60:40 | L(D) | 22.2 | 32.2 | 35.4 | 0.1376 | 73.6 |
| 50:50 | DL | 15.6 | 19.4 | 26.4 | 0.097 | 59.5 |

Cond. $5 \cdot 10^{-4}$ M $MnSO_4 \cdot H_2O$, $2.5 \cdot 10^{-4}$ M ascorbic acid, 0.5 M L-Arg, [E] = 9990 Units/(l · mol L-Arg), $[S]_o/[E] = 1.63 \cdot 10^6$, starting pH: 11.5

With the kinetic results, the rate equation of the arginase reaction reads (Equation 6):

$$r = \frac{V_{max}[\text{L—Arg}]}{K_M(1 + [\text{L—Orn}]/K_{pi})(1 + [\text{D—Arg}]/K_{i,D-Arg}) + [\text{L—Arg}]}$$

Selectivity of arginase

Enantioselectivity of arginase: D-Arg is neither a substrate of arginase nor a non-competitive inhibitor (FIG. 3); the other main condition for using the arginase reaction for the preparation of D-Arg is sufficiently high enantioselectivity of the enzyme. In a 50:50-mixture of D- and L-Arg, the formation of L-Orn as well as D-Orn was followed by chiral HPLC directly from the reacting solution at different degrees of conversion to test, the enantioselectivity of calf liver arginase. At no degree of conversion could D-Orn be detected in the solution. To allow calculation of the E-value which characterizes enantioselectivity according to equation (3) the limit of detection of 1.0% of D-Orn next to L-Orn was taken as the maximum possible D-Orn content to obtain a minimum E-value of 460, i.e. calf liver arginase can be regarded as highly enantioselective. Since the e.e. (enantiomeric excess) of both isolated D-Arg and L-Orn products was higher than 99.8%, the enantioselectivity of calves' liver arginase is likely to be even higher than determined with the above-described HPLC method straight from the reaction mixture.

Temperature stability: To assess the storage stability of arginase and to investigate the influence of temperature on the stability as well as the role of ascorbic acid as a stabilizer of arginase, deactivation curves were measured at different temperatures. The data in Table 3 reveal that, at all investigated temperatures in the range of −25° to 60° C., calves' liver arginase deactivates by a simple exponential decay law:

$$[E]_{active,t} = [E]_{active,o}\, exp\, (-k_{des} \cdot t)$$

The corresponding half-time of deactivation, $\tau_{1/2}$, after which 50% of the initial activity remain, can be calculated by $\tau_{1/2} = \ln 2/k_{des}$.

Figure 5:
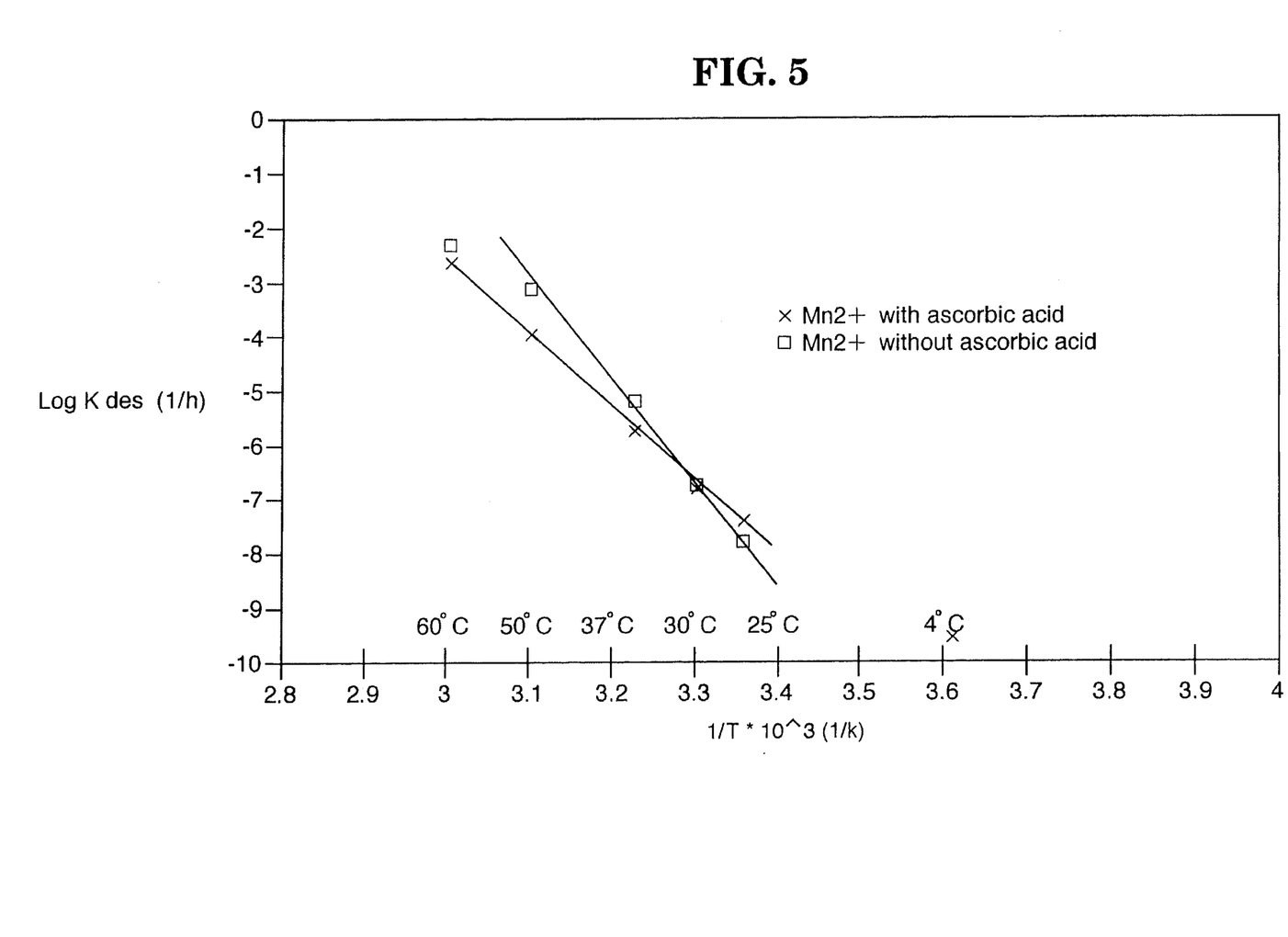
FIG. 5 is a plot of $k_{des}$ vs. 1/T.

Below room temperature, arginase is stable over several months if both manganese ions and ascorbic acid are added. In the range of temperatures typical for processing, stability is sufficient ($\tau_{1/2}$ at 25° C. is 70 days). However, even at slightly elevated temperatures, arginase deactivates rapidly: $\tau_{1/2}$ at 37° C. is only nine days. Without the initial addition of ascorbic acid, the enzyme deactivates significantly faster. The stabilization of arginase at temperatures higher than 25° C. through the addition of ascorbic acid is reflected in a lower free enthalpy of deactivation $\Delta G^{\ddagger}$. The activation parameters $\Delta G^{\pm}$, $\Delta H^{\pm}$ and $\Delta S^{\pm}$ are obtained from a ln $(k_{deact}/T)$ vs. 1/T plot (FIG. 5) by taking logarithms of the expression for $k_{deact}$ from the theory of absolute rates $$k_{deact}=(kT/h)\cdot exp[-(\Delta G^{\pm})/RT](kT/h)\cdot exp[-(\Delta H^{\pm}-T\Delta S^{\pm})/Rt \quad (7a);$$

$$ln(k_{deact}/T)=ln(k/h)+\Delta S^{\pm}/R+\Delta H^{\pm}/RT \quad (7b)$$

From the slopes of the $ln(k_{deact}/T$ vs 1/T) plot, $\Delta H^{\pm}$ in the presence of ascorbic acid is $-117.1\pm2.4$ kJ/mol (25°–60° C.; $r^2=0.9988$), if stabilizer is absent $\Delta H^{\pm}$ equals $-138.1\pm5.2$ kJ/mol (30°–60° C.; $r^2=0.9972$); from tile intercepts, $\Delta S^{\pm}$ is calculated to be $+15.8\pm0.7$ J/mol·K in tlhe presence and $+87.7\pm1.2$ J/mol·K in the absence of ascorbic acid. At 298K (25° C.), the difference in $\Delta G^{\pm}$ is minimal ($-112.0$ (no ascorbate) vs. $-112.4$ kJ/mol) while at 333K (60° C.),$\Delta\Delta G^{\pm}$ is substantially larger at 2.9 kJ/mol ($-108.9$ vs $-111.8$ kJ/mol). The data for $k_{deact}/T$ at temperatures lower than 25° C. in the presence of stabilizer do not follow equation (7), so that identity of the mechanism of deactivation most likely holds for $T\geq298K$ only. The significance of stbailization of arginase by ascorbate for the operational stability of the enzyme during reaction cannot be shown by comparing $\Delta G^{\pm}$'s but must be elucidated with a test of operational stability.

Operational enzyme stability: On both a laboratory scale (10 ml) and a pilot scale (12 l) operational stability of arginase was determined with enzyme-membrane CSTRs. Since replenishing lost enzyme activity would have meant the addition of very small amounts of enzyme on a lab scale, both enzyme activity consumption per unit mass (kg) of L-Orn product as well as the deactivation rate constant $k_{des}$ under operating conditions were determined from conversion-residence time-profiles (Table 4). If active enzyme concentration at time t, [E]t, is assumed to be proportional to the degree of conversion at that time, $x_t$, $k_{des}$ can be calculated with the exponential decay law (equations (8) and (9)):

$$x_{t2}/x_{t1}=[E]_{t2}/[E]_{t1}=exp\{(-k_{des}\cdot(t_1-t_2)\} \quad (8)$$

or $$k_{des}=-\{log(x_{t2}/x_{t1})\}/(t_1-t_2) \quad (9)$$

Enzyme consumption per unit mass of product (EC/kg L-Orn) is determined from the slope of conversion vs. residence time at maximum conversion, U/h, as well as residence time $\tau_6$ initial substrate concentration $[S]_o$ and maximum conversion $x_{max}$ (Equation 10):

$$EC(U/kg\ L\text{-}Orn)=(U/h)(1000/MW_{L\text{-}Arg})/(\tau\cdot[S]_0\cdot x_{max}) \quad (10),$$

Values for both $k_{des}$ and EC/product mass are listed in Table 4.

TABLE 4 enzyme consumption numbers for the arginase reaction

| Scale | agitation | stabilizer [Asc.a.](M) | pH | oper. stab. (U/kg L-Orn) | $k_{des}$ (hrs$^{-1}$) |
|---|---|---|---|---|---|
| 10 ml | 200/min | $5\cdot10^{-4}$ | 10.5 | 15800 | $3.7\cdot10^{-2}$ |
| 10 ml | 200/min | $2.5\cdot10^{-4}$ | 9.5 | 5460 | $3.8\cdot10^{-2}$ |
| 12 l | recycle | 0 | 9.5 | 5890 | |

TABLE 4-continued

| | ($\tau=$ 3 hrs) | | | |
|---|---|---|---|---|
| 12 l | no | 0 | 9.5 | 5000 |
| 12 l | no | $2.5\cdot10^{-4}$ | 9.5 | 270 |

Cond: $5\cdot10^{-4}$ M MnSO$_4$.H$_2$O, ascorbic acid as indicated, 0.75 M L-Arg, [E] = 10 k Units/(l · mol L-Arg.), $[S]_o/[E] = 1.63\cdot10^{-6}$, indicated pH-value is pH of product solution measured at maximum conversion.

The numbers for $k_{des}$ at 25° C. from operational stability measurements ($3.8\cdot10^{-3}$ hrs$^{-1}$; Table 4) and temperature stability measurements ($4.1\cdot10^{-4}$ hrs$^{-1}$) suggest that during the arginase reaction the enzyme is deactivated primarily by mechanical effects from stirring or, more likely, by irregular or insufficient supply of manganese activator and not by temperature effects. From the results in the pilot unit it is concluded that, while stopping mechanical agitation results in a decrease of enzyme deactivation, the stabilizing effect of adding ascorbic acid achieves the main improvement in consumption of enzyme units.

Other potential causes of arginase instability: Tests of arginase activity in a sequence of batches in the presence of polysulfone and regenerated cellulose membrane materials as well as no membrane for control revealed no difference in enzyme stability. Likewise, addition of large amounts of solid MnO$_2$ to arginase solution to test susceptibility to solid precipitates did not cause change in activity during a sequence of four batches.

Figure 6A:
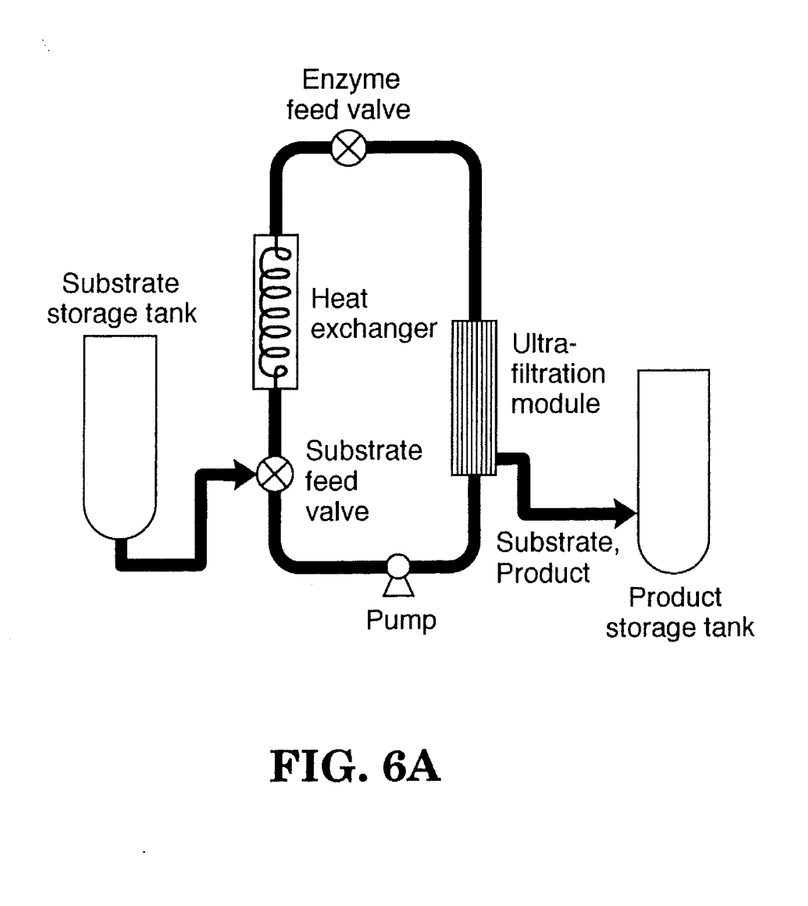
FIG. 6 contains schematic illustrations of apparatus useful for the process of the invention.
Figure 6B:
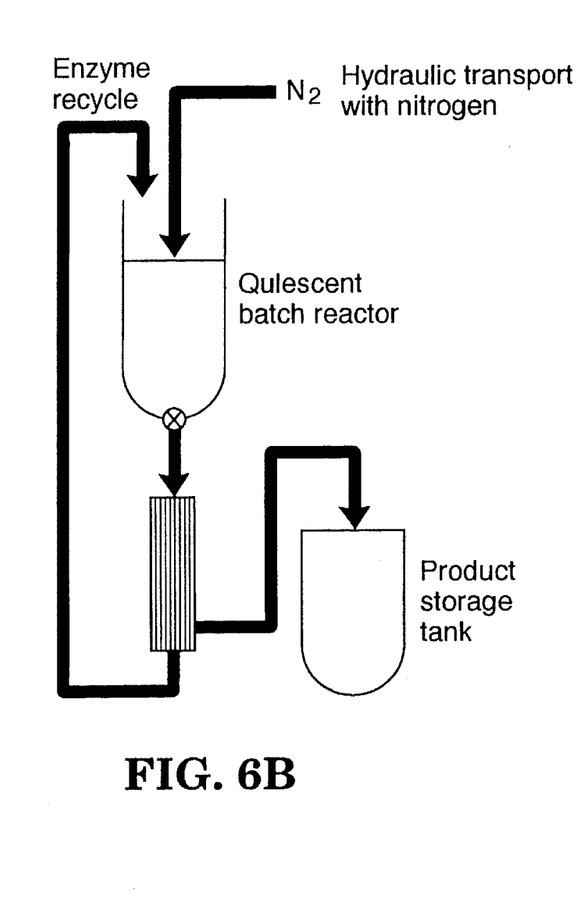

Since arginase was found to be sensitive to mechanical agitation it was decided not to employ the usual recycle reactor arrangement with continuous pumping on the pilot scale. Instead, a batch-UF-reactor configuration was chosen: the reaction was carried out in a quiescent medium to avoid mechanical agitation while the medium was conveyed hydraulically to charge the reactor and to separate the enzyme over a UF membrane after completion of a batch for reuse in the next batch (FIG. 6). Since residence time could not be determined in this set-up $k_{des}$ could not be calculated. Instead, enzyme unit consumption data based on the amount of L-Orn produced were taken for comparison with conditions on the lab scale.

Arginase in a pumped solution is found to be unstable at an initial pH of 9.5 with Mn$^{2+}$ but no ascorbic acid added: conversion after 24 hours decreased from 53% to zero after five runs. Somewhat surprisingly, enzyme stabilized by addition of half-equimolar ascorbic acid to Mn$^{2+}$ in the lab-scale reactor at pH 9.5 deactivated almost as fast as the unstabilized solution in the pilot-scale reactor (5460 vs. 5890 U/kg L-Orn). Reaction in a quiescent medium protected the enzyme somewhat, so that 8% conversion (down from 60%) remained after eight batches (5000 U/kg L-Orn). At a pH of 9.5 in the quiescient recycle loop, the enzyme was almost stable (88% to 63% conversion) within twelve runs at half-equimolar addition of ascorbic acid to Mn$^{2+}$-ions (270 U/kg L-Orn).

The invention is illustrated by the following additional examples:

EXAMPLE 11

1.74 g DL-arginine (50:50) were dissolved in 10 ml water and mixed with 0.21 mg manganese sulfate.H$_2$O, 0.11 mg ascorbic acid and 0.5 mg calf liver L-arginase (Boeringer Mannheim, 97 U/mg). The progress of the reaction was followed with HPLC (amino column; mobile solvent 65:35 acetonitrile:phosphate buffer (pH 6.4). After 6 hours at 25° C., 50% of the original amount of arginine had reacted and a corresponding amount of ornithine had been formed (conversion 100%).

The two products were isolated (ornithine as acetate) and checked for enantiomeric purity via enantiospecific columns (arginine: HPLC column, ornithine: GC column).
Arginine: isolated yield: 0.81 g (93%), D-component>99.9%
Ornithine: isolated yield: 0.57 g (87%), L component>99%

EXAMPLE 12

100 ml of a 1.25 molar, racemic solution of DL-arginine are mixed with $5 \cdot 10^{-4}$ mol/l $MnSO_4 \cdot H_2O$, $2.5 \cdot 10^{-4}$ mol/l ascorbic acid and 14.0 mg L-arginase (=10000 U/(l·mol L-Arg)). After 22 hours, the conversion was 50% of the original amount of arginine and a corresponding amount of ornithine had been produced.
Arginine: isolated yield: 10.98 g (100.9% of theory), D-component (HPLC): >99.9%
Ornithine: isolated yield: 11.47 g (95.6% of theory), amount of rotation $[\alpha]_3^{20}$: +9.8 (theory 9-10, c=5/100 ml $H_2O$)

EXAMPLE 13

A procedure analogous to that of Example 12 was used, except that the D:L ratio in the arginine was 25:75 and 12.9 ml L-arginase (=10000 U/(l·mol L-Arg)) were used. After 42 hours, 25.3% of the original amount of arginine had reacted, that is, the conversion was 99.6%. The products were worked up as described above.
Arginine: isolated yield: 5.2 g (96.3% of theory), D-component (HPLC): >99.9%
Ornithine: isolated yield: 15.2 g (87.9% of theory), amount of rotation $[\alpha]_D^{20}$: +9.5 (theory 9-10, c=5/100 ml $H_2O$)

What is claimed is:

1. A method for the preparation of D-arginine which comprises an enzymatic conversion of DL-arginine, in the presence of an L-arginase which selectively converts the L-arginine in DL arginine into L-ornithine, in an aqueous reaction medium, said method comprising the steps of:
    a) adjusting the pH of said aqueous reaction medium to a range between 8.0 and 10.0 prior to the enzymatic conversion with an acid;
    b) maintaining the pH between 8.0 and 10.0 during the enzymatic conversion with the same acid used in step (a);
    c) adjusting the pH of said aqueous reaction medium after said enzymatic conversion to a range between 6.5 and 7.0;
    (d) allowing an L-ornithine salt to crystallize from said aqueous reaction medium and recovering D-arginine.

2. The method as set forth in claim 1 in which the enzyme is separated by ultrafiltration from the reaction mixture at the end of the enzymatic conversion.

3. The method as set forth in claim 1 in which the L-arginase is obtained from beef liver or calf liver.

4. The method set forth in claim 1 further comprising the step of recovering crystals of the L-ornithine salt.

5. The method set forth in claim 4 further comprising the step of removing the L-arginase from the reaction medium by ultrafiltration prior to crystallization of the L-ornithine salt.

* * * * *